US005136656A

United States Patent [19]

Frederiksen et al.

[11] Patent Number: 5,136,656

[45] Date of Patent: Aug. 4, 1992

[54] PROBE MICROPHONE

[75] Inventors: Erling Frederiksen, Holte; Ole Schultz, Copenhagen, both of Denmark

[73] Assignee: Aktieselskabet Bruel & Kjaer, Naerum, Denmark

[21] Appl. No.: 529,454

[22] Filed: May 29, 1990

[30] Foreign Application Priority Data

May 29, 1989 [DK] Denmark ............................ 2624/89

[51] Int. Cl.$^5$ ........................ H04R 29/00; A61B 1/22; A61B 7/02

[52] U.S. Cl. ........................................ 381/56; 73/585; 181/131

[58] Field of Search ................ 381/56, 168, 169, 68.6; 73/585, 587, 589, 574, 591, 645, 648; 367/140, 152; 181/131, 158

[56] References Cited

U.S. PATENT DOCUMENTS 2,085,130 6/1936 Swickard ........................... 181/158
2,228,886 1/1938 Olson ................................. 367/152
2,939,922 6/1956 Gorike ............................... 181/158
4,029,083 6/1977 Baylor ................................. 73/585
4,270,627 6/1981 Hill ..................................... 181/131
4,677,679 6/1987 Killion ............................... 381/68.6

*Primary Examiner*—James L. Dwyer
*Assistant Examiner*—Jack Chiang
*Attorney, Agent, or Firm*—Cushman, Darby & Cushman

[57] ABSTRACT

A probe microphone comprising an acoustic transducer with a cavity, to which a probe tube and a matching tube are connected. The matching tube is divided into several small tubes of a total internal transverse cross sectional area substantially corresponding to the internal transverse cross sectional area of the probe tube. The small matching tubes improve the frequency response because of their acoustic loss. Moreover, a further improvement is achieved when the matching tubes are of different lengths, the already reflected signals thereby outbalancing each other. As a result, a probe microphone with a more uniform frequency response than previously known is achieved.

6 Claims, 4 Drawing Sheets

Free field frequency characteristics for Type 4184

Free field frequency characteristics for Type 4184

PROBE MICROPHONE

FIELD OF THE INVENTION

The invention relates to a probe microphone comprising an acoustic transducer with a cavity to which a probe tube and an impedance-matching tube are connected.

BACKGROUND OF THE INVENTION

A probe microphone must be able to measure the sound pressure at a point for instance in a very hot environment. An oblong probe tube in connection with a microphone cartridge, gives, however, some unwanted resonances. It has been attempted to solve this problem by means of an almost infinitely long tube to which a branch tube is connected, the branch tube being connected to a cavity and a microphone cartridge. As a result, unwanted resonances in a portion of the frequency interval are reduced. However the microphone cartridge and the associated attachment is an unwanted load, especially at high frequencies.

SUMMARY OF THE INVENTION

The object of the invention is to provide a probe microphone with a more uniform frequency response.

The probe microphone according to the invention is characterized in that the impedance matching tube is divided into several small tubes having a total transverse cross sectional area substantially corresponding to the transverse cross sectional area of the probe tube. The small impedance-matching tubes improve the frequency response because of their greater acoustic loss. Moreover, a further improvement is achieved if the impedance-matching tubes are of different lengths, the already reduced reflections partly outbalancing each other.

BRIEF DESCRIPTION OF THE DRAWINGS

The invention is described in greater detail below with reference to the accompanying drawings, in which.

DESCRIPTION OF PREFERRED EMBODIMENTS

Figure 2:
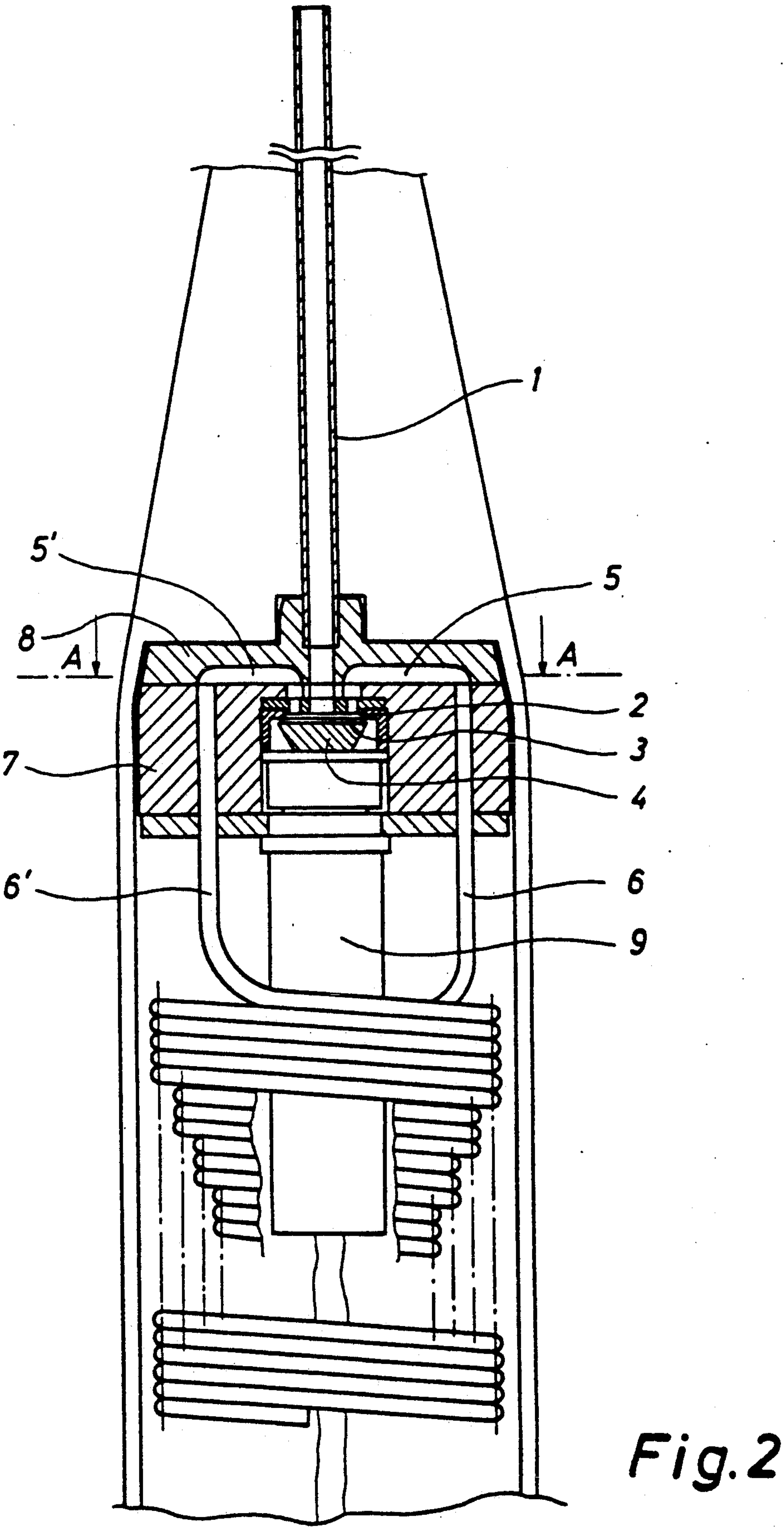
FIG. 2 illustrates the upper portion of the probe microphone on, a large scale.
Figure 3:
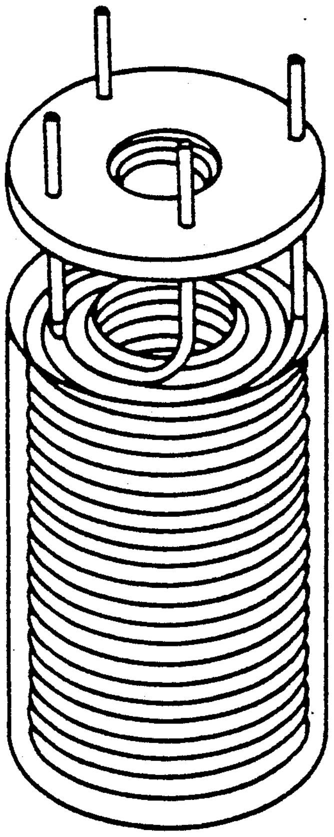
FIG. 3 is a perspective view of the associated impedance-matching tubes.

The probe microphone of FIG. 2 comprises a probe tube 1. The probe tube 1 has an internal diameter of approximately 3.1 mm and a length of approximately 174 mm. The probe tube 1 extends into a circular cavity 2 in front of the diaphragm by a condensator microphone. The cavity 2 is approximately 25.5 $mm^3$. The diameter of the cavity 2 is approximately 9.3 mm. A frustoconical back electrode 4 is placed below the diaphragm 3. Four grooves 5, 5', of which only two are shown, extend from the cavity 2. The grooves 5, 5' continue into separate tubes 6, 6'. The tubes 6, 6' have a length of 2,480 mm, 2,790 mm, 3,160 mm and 3,525 mm. respectively. Each of these tubes 6, 6' has a length of at least 14.25 times as long as the probe tube. The tubes, 6, 6' are placed at the same angular distance in relation to the cavity 2. The internal diameter of the tubes is approximately 1.55 mm except where the tubes 6 6' extend into the cavity 2, two small holes being adapted to provide a good matching. The impedance-matching tubes 6, 6' have a total internal transverse cross-section area within a range of 0.9375–1.00 times the internal transverse cross-section area of the probe tube. The impedance-matching tubes 6, 6' are carried through a solid body 7 to horizontal grooves 5, 5' in the upper body 8. The impedance-matching tubes 6, 6' are twisted around a common core and embedded as shown in FIG. 3.

As mentioned above, the condensator microphone comprises a frustoconical back electrode 4, placed in a cavity behind the diaphragm 3. The back electrode 4 is fastened to an insulator (not shown). The microphone housing is the second electrode. The rest of the microphone body (the microphone cartridge) is seen below the frustoconical back electrode 4. A switch is provided in the bottom of the cartridge, this switch being connected to a pre-amplifier 9 placed inside the reel of twisted impedance-matching tubes 6, 6'.

Figure 1:
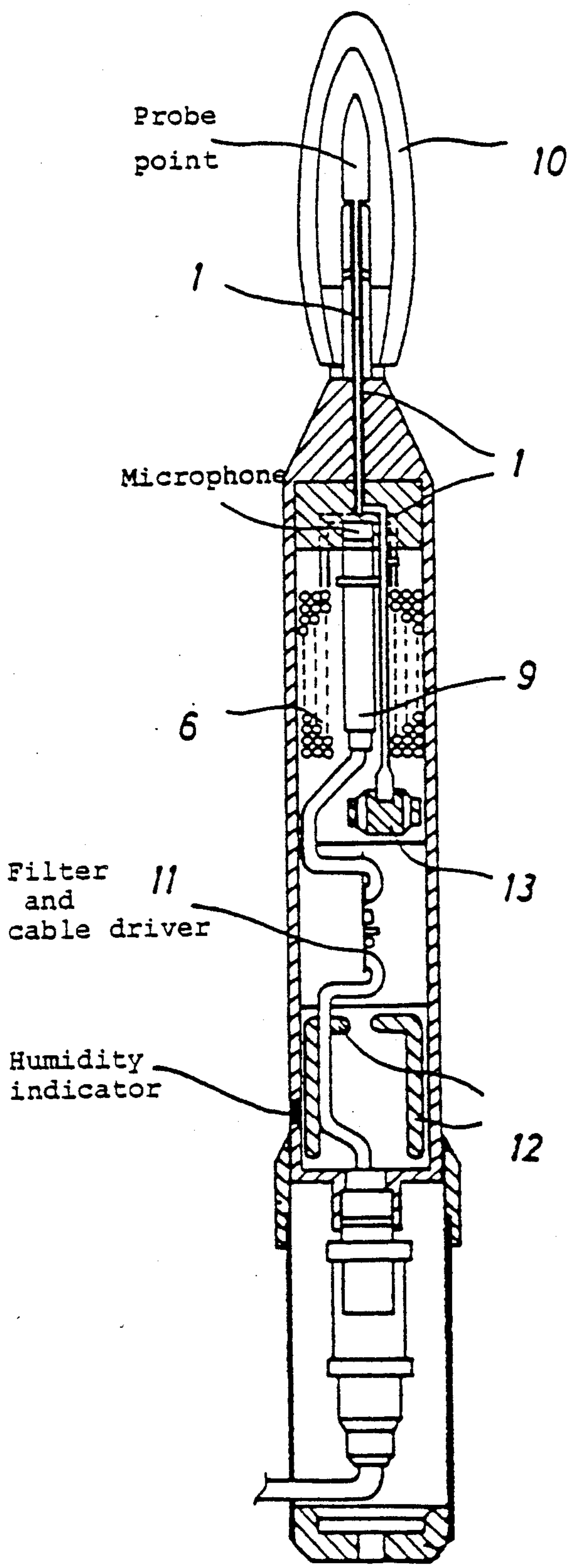
FIG. 1 illustrates a probe microphone according to the invention.

FIG. 1. shows the entire probe microphone. A wind screen 10 is seen on top. The wind screen 10 is made of foam material with open pores. The foam material is transparent to sound. Measuring the wind noise which might exist around a detached microphone is of no interest. The wind screen 10 reduces the air flow and consequently, the wind-induced noise. The probe tube 1 extends to the microphone, from where the signal is transmitted to the pre amplifier 9. An electric voltage is used for electrical calibration of the system.

The measuring body influences the acoustic field to be measured. A measurement of the field without the presence of the microphone is required because the microphone influences the field. Also, the probe system has a frequency response deviating from a flat frequency response. The latter also influences the system. The frequency response of the microphone is not flat, either. A filter 11 compensates for all the above factors. An adaptation for achieving a low output impedance is provided by a cable driver in such a manner that relatively long cables can be drawn. The entire container is encapsuled, and is kept dry for reasons of dependability by means of a dehumidifier 12. It is indicated when the dehumidifier 12 is used up.

The microphone is placed on a post or pole. A pole is raised and a screw cap is screwed onto the top of the pole, whereby the entire microphone unit becomes part of the pole. In this manner, the sound field is disturbed as little as possible. Alternatively the microphone may be placed on a tripod. A special adaptor must be provided in order to fasten the microphone to the tripod.

It is preferred to calibrate with a known sound pressure to check if the microphone responds in the proper manner. It is, however not possible to provide a sufficiently good sound source. The test sound source 13 serves to provide a relatively known sound in order to check if there is sound passage in the system.

Figure 4:
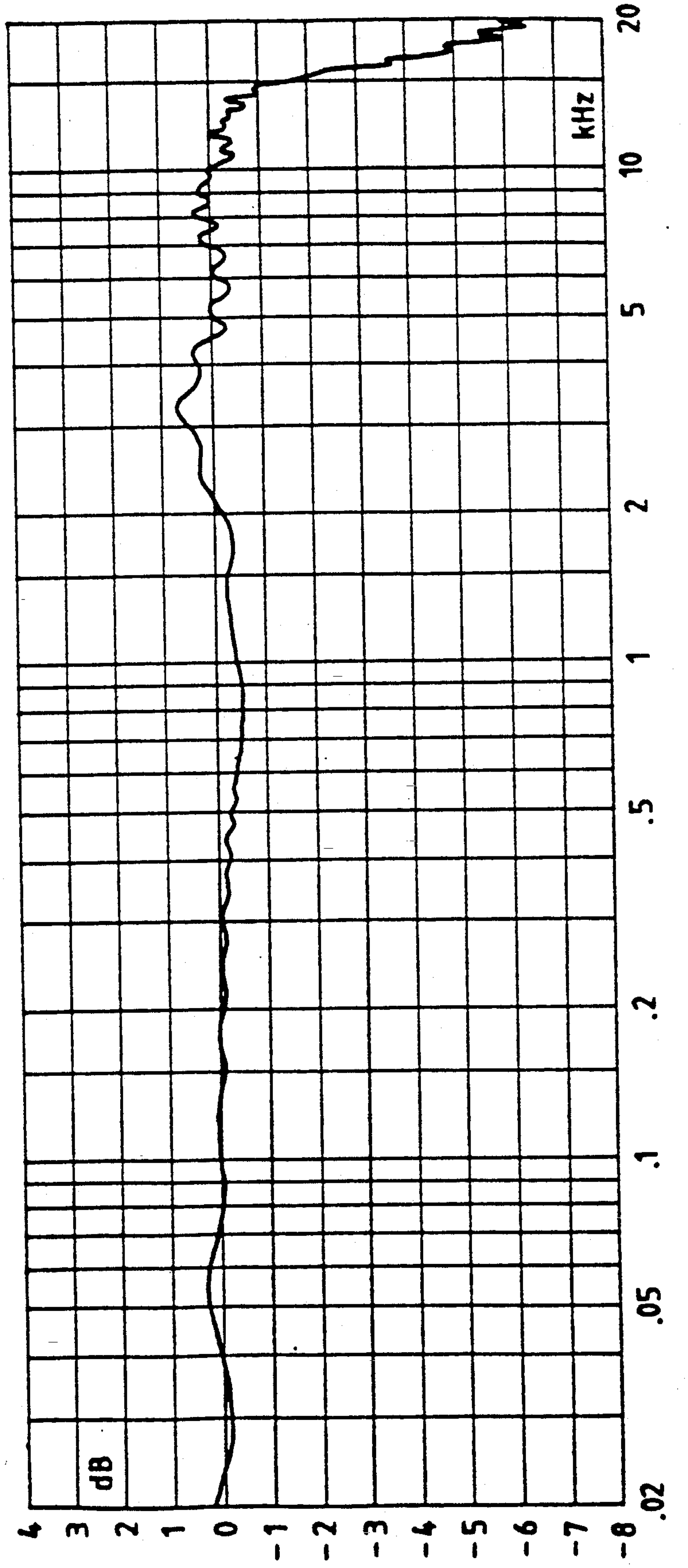
FIG. 4 illustrates the frequency response of the probe microphone.

FIG. 4 shows an example of free field characteristics of the probe microphone of FIG. 1. The curve is almost flat in the interval 20–15 kHz. The use of several small matching tubes having different lengths improve especially the frequency response, especially in the area below 5 kHz. Where the microphone is connected there is no impedance completely matching the impedance of the probe tube 1. A discontinuity therefore causes reflections at higher frequencies. The fluctuations of the response at the high frequencies are, however relatively small, which is due to the form of the cavity 2 as a flow is carried through the cavity 2 in such a manner that the cavity forms part of the tube. The unwanted reflections at high frequencies are thereby reduced.

The condensator microphone may be replaced by another pressure-measuring transducer, for instance based on a ceramic member.

We claim:

1. A probe microphone, comprising:

an acoustic transducer having means defining a cavity therein;

a probe tube having a given internal transverse cross-sectional area; said probe tube having one end communicated with said cavity;

a plurality of impedance-matching tubes each having a given internal transverse cross-sectional area; said impedance-matching tubes each being longer than said probe tube, and together having a total internal transverse cross-sectional area which is substantially equal to that of said p robe tube;

said impedance-matching tubes each being different in length relative to one another, there being a total of four said impedance-matching tubes, which are respectively 2,480, 2,790, 3,160 and 3,525 mm in length.

2. A probe microphone, of claim 1 wherein:

said impedance-matching tubes each being different in length relative to one another, there being a total of four said impedance-matching tubes, and each has an internal diameter of about 1.55 mm.

3. A probe microphone, comprising:

a body containing an acoustic transducer having a diaphragm with one side thereof exposed to a cavity provided within the body;

a probe tube having a given internal transverse cross-sectional area; said probe tube extending outwards from said body and having one end communicated through said body with said cavity on said one side of said diaphragm;

a plurality of impedance-matching tubes each being at least 14.25 times as long as said probe tube; each probe tube having a given internal transverse cross-sectional area; said impedance-matching tubes together having a total internal transverse cross-sectional area which is within a range of 0.9375 to 1.00 times the internal transverse cross-sectional area of said probe tube; each said impedance-matching tube extending outwards from said body and having one end communicated through said body with said cavity on said one side of said diaphragm.

4. The probe microphone of claim 3, wherein:

there are four said impedance-matching tubes;

said body is housed in a housing out through which said probe tube projects; and said impedance-matching tubes are coiled within and terminate within said housing.

5. The probe microphone of claim 4, wherein:

said impedance-matching tubes are coaxially coiled about a common core; said probe has an internal transverse cross-sectional diameter of approximately 3.1 mm; said impedance-matching tubes each have an internal cross-sectional area of approximately 1.55 mm; said probe is approximately 174 mm long; and said impedance-matching tubes are respectively 2,480, 2,790, 3,160 and 3,525 mm long.

6. The probe microphone of claim 5, wherein:

said acoustic transducer is a condensator microphone having a back electrode located on an opposite side of said diaphragm from the side which is exposed to said one end of probe tube and impedance-matching tubes.

* * * * *